United States Patent [19]

Bentov

[11] 4,320,762
[45] Mar. 23, 1982

[54] DILATOR

[76] Inventor: Itzhak E. Bentov, 241 Glezen La., Wayland, Mass. 01778

[21] Appl. No.: 114,061

[22] Filed: Jan. 21, 1980

Related U.S. Application Data

[60] Continuation of Ser. No. 27,299, Apr. 5, 1979, abandoned, which is a division of Ser. No. 781,183, Mar. 25, 1977, Pat. No. 4,684,709, which is a continuation-in-part of Ser. No. 625,314, Mar. 10, 1975, abandoned.

[51] Int. Cl.³ .................. A61M 29/00; A61M 16/00
[52] U.S. Cl. ..................................... 128/343; 128/345
[58] Field of Search .................... 128/341–345, 128/242–244, 303.11, 303.12, 356, 361, 400, 403

[56] References Cited

U.S. PATENT DOCUMENTS

| | | | |
|---|---|---|---|
| 972,983 | 10/1910 | Arthur | 128/345 |
| 1,328,624 | 1/1920 | Graham | 128/345 |
| 1,737,488 | 11/1929 | Zohlen | 128/341 |
| 2,499,761 | 3/1950 | Kraemer | 128/341 |
| 2,621,651 | 12/1952 | Wallace | 128/343 X |
| 3,557,794 | 1/1971 | Van Patten | 128/243 X |
| 3,667,474 | 6/1972 | Lapkin et al. | 128/345 |
| 3,968,800 | 7/1976 | Vilasi | 128/343 |

*Primary Examiner*—Stephen C. Pellegrino
*Attorney, Agent, or Firm*—Wolf, Greenfield & Sacks

[57] ABSTRACT

A dilator comprising a housing and an elongated, slotted probe or core biased and slideable relative to the housing. The core carries expandable leaves or ribs, each having wedges disposed therealong. The wedges engage slots of the core and when the core is moved relative to the leaves the leaves move to their expanded position. In one embodiment biasing means are provided within the housing for biasing the core to its expanded position and a preferably soluble wax block is used in the housing for compressing the biasing means. With this arrangement when the dilator is inserted in the patient the wax dissolves over a period of hours and the biased core is released to thereby cause gradual, painless expansion of the body opening. In a preferred embodiment a remote actuator couples by cable means to the core of the dilator for operating the dilator. In this embodiment a biasing means is provided in the remote actuator instead of the housing of the dilator.

21 Claims, 24 Drawing Figures

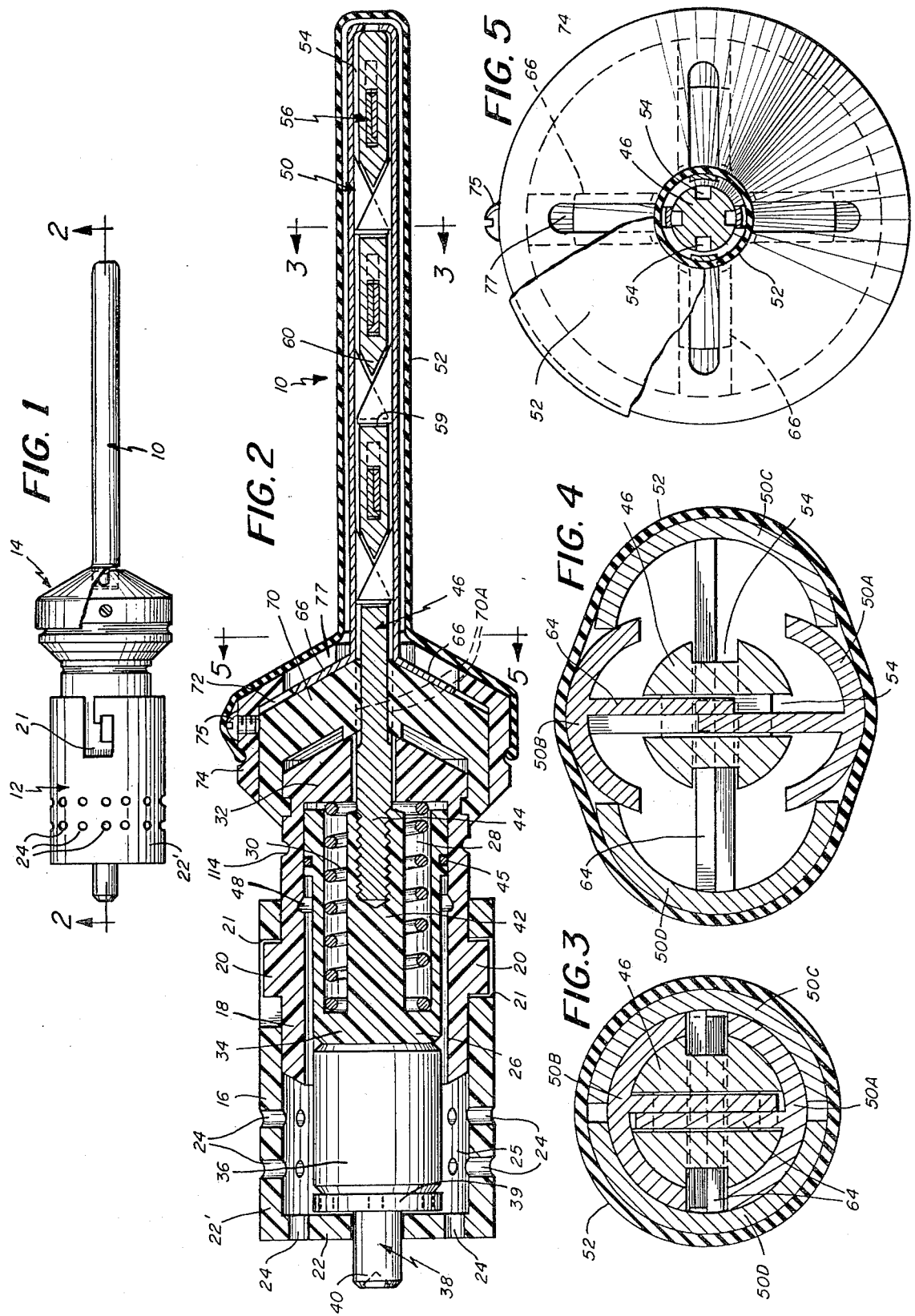

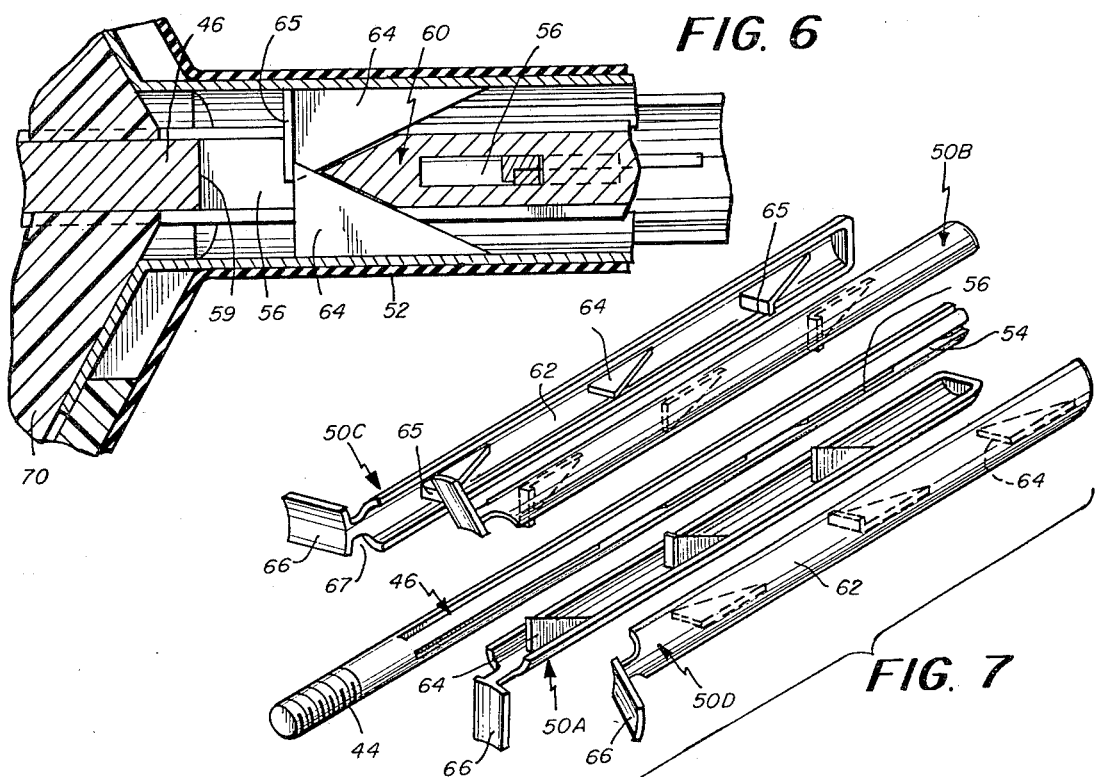
FIG. 6
FIG. 7
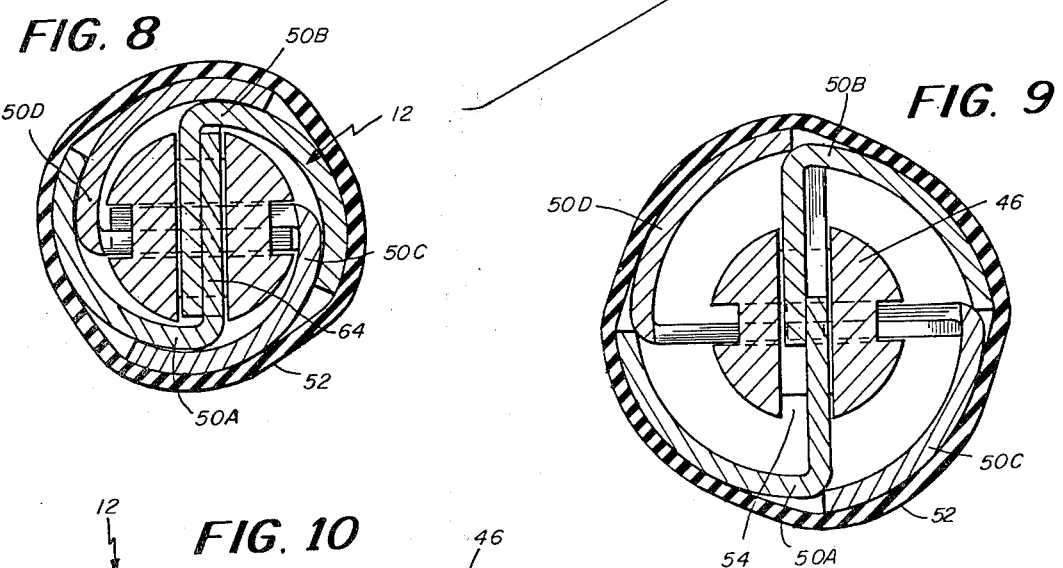
FIG. 8
FIG. 9
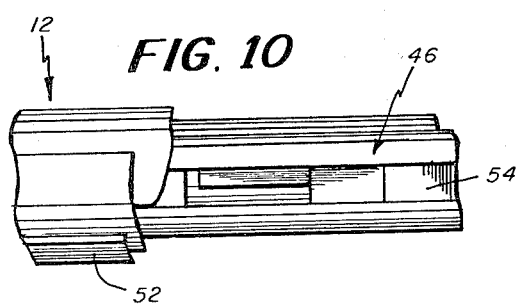
FIG. 10

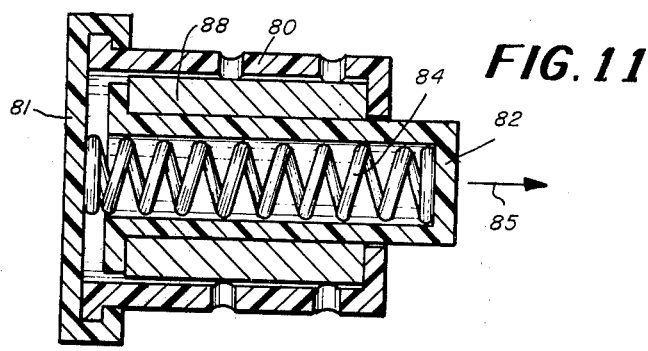
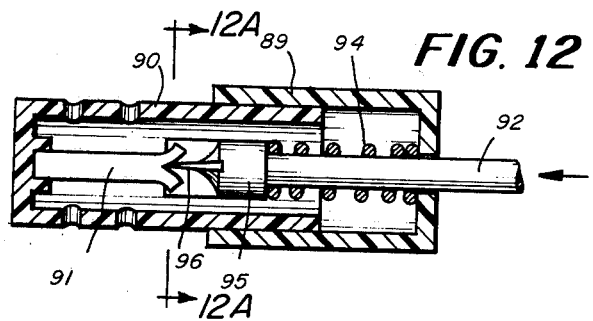
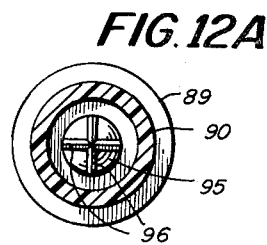
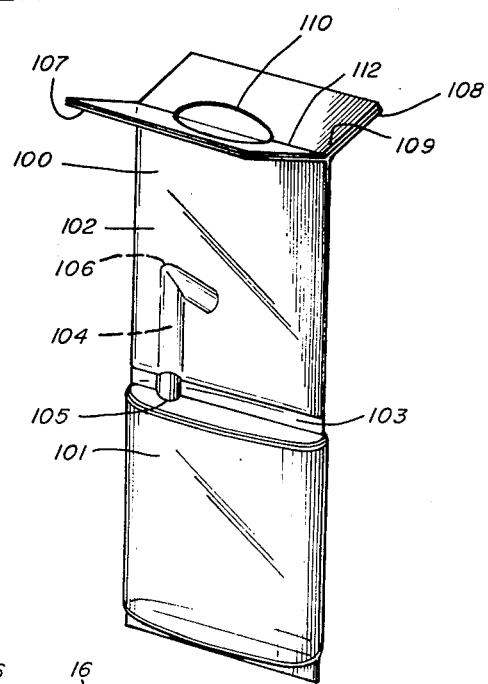
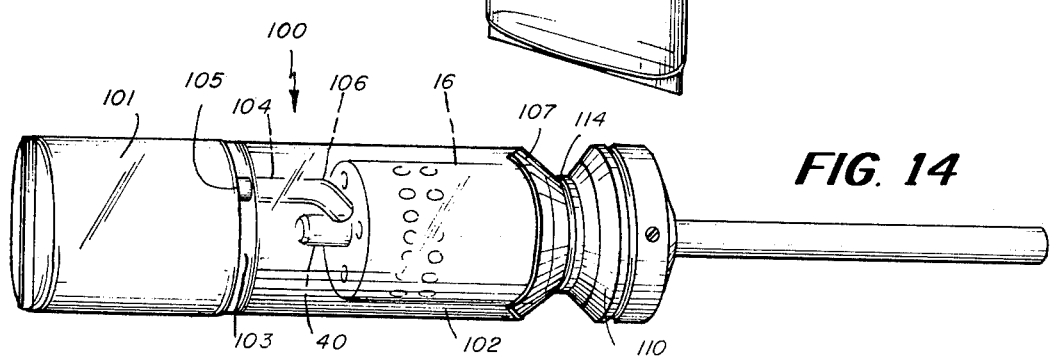

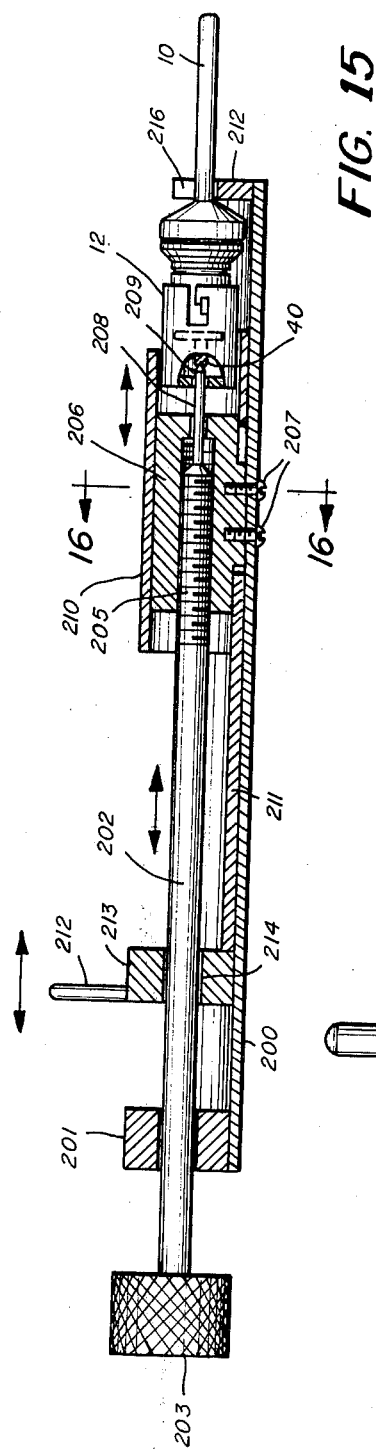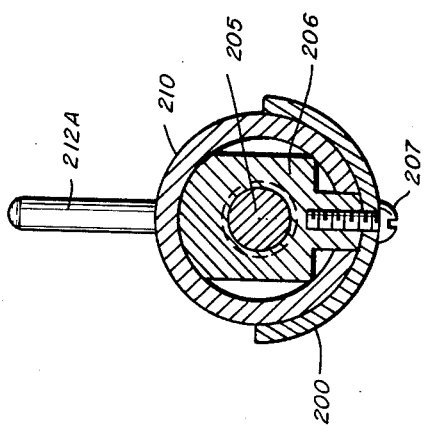

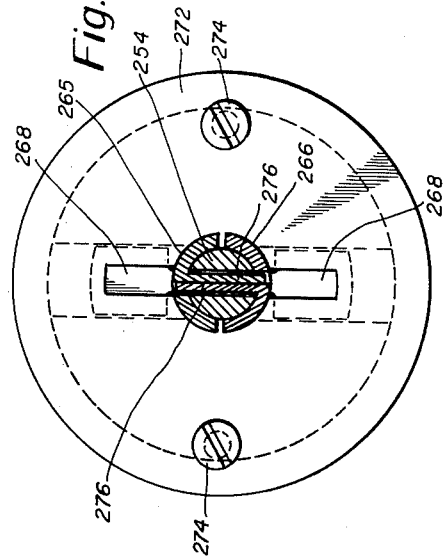
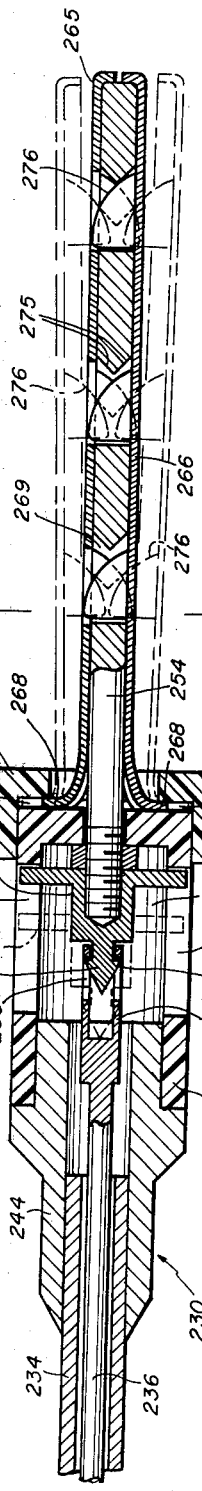
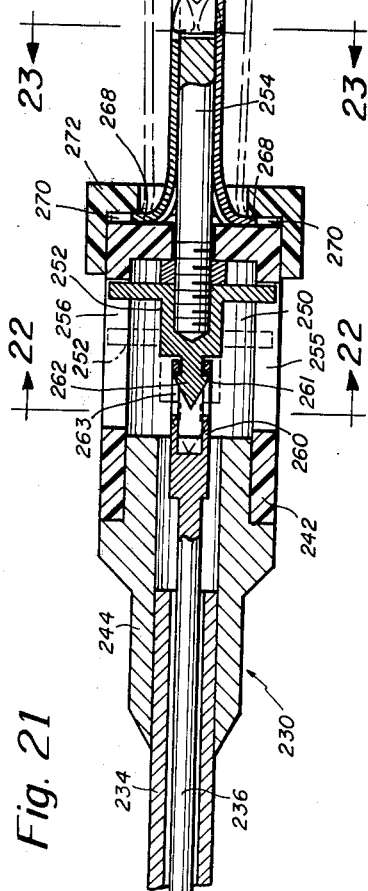
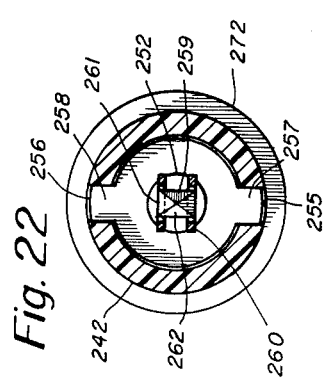

DILATOR

RELATED APPLICATION

This is a continuation of application Ser. No. 27,299, filed Apr. 5, 1979, now abandoned, which, in turn, is a division of application Ser. No. 781,183, filed Mar. 25, 1977, now U.S. Pat. No. 4,684,709, which, in turn, is a continuation-in-part application of Ser. No. 625,314, filed Mar. 10, 1975, now abandoned.

BACKGROUND OF THE INVENTION

The present invention relates in general to dilators and in particular to dilators that are for use in the cervix. With one embodiment of the present invention the dilator is inserted into the patient for use over a relatively long period of time such as a few hours for expanding the cervix with minimal pain. In a preferred form of the invention the dilator couples to a remote actuator having means for controlling gradual opening of the dilator.

The prior art discloses dilators in the following U.S. Pat. Nos. 1,331,737; 1,605,894; 3,312,222; 3,557,794; and 3,789,852. It is one purpose of the present invention to provide a cervical dilator that is of improved operation in comparison with existing dilators and one which may be operated incrementally to expand the dilator very gradually to minimize the degree of pain for the patient.

One object of the present invention is to provide a cervical dilator that may be left in the patient for operation over a relatively long period of time, such as a few hours, to expand the cervix.

Another object of the present invention is to provide a cervical dilator that is relatively easy to use and that can be used with little discomfort to the patient.

A further object of the present invention is to provide a cervical dilator that operates in combination with a remote actuator coupled by cable means to the dilator for expanding the dilator relatively slowly under controlled expansion conditions.

Still another object of the present invention is to provide a cervical dilator that is relatively simple in construction, that is easy to assembly and fabricate, and that can be made relatively inexpensively.

A further object of the present invention is to provide a dilator which expands to a maximum dimension essentially in a single step. Since conventional dilators require many insertions before the desired dilation is obtained, the risk of infection is increased with these conventional dilators. However, with the dilator of this invention the single step operation minimizes the risk of invention. Also, the dilator of this invention is adapted to be used with a sterile disposable sleeve, which makes the need for re-sterilization optional.

SUMMARY OF THE INVENTION

To accomplish the foregoing and other objects of this invention, there is provided a dilator which comprises an elongated probe means or core which is partially contained within and extending from a housing. This probe means is biased preferably into the chamber defined by the housing. In one embodiment a compression spring is disposed in the chamber for biasing the probe means. In a preferred embodiment the probe means is operated from a remote actuator which couples to the probe means by means of an actuating cable. In accordance with the invention the probe means includes an elongated core, an expandable outer shell, and means associated with the core and shell for causing the shell to expand upon relative movement between the core and shell. In one embodiment the shell comprises four elongated leaves while in the preferred embodiment only a pair of elongated leaves are used. The pair of elongated leaves are diametrically disposed about the core. The shell is prevented from having any substantial longitudinal movement relative to the housing. The core, on the other hand, is movable relative to the housing and shell to cause the shell to expand as the core is drawn into the housing. In an alternate embodiment the core may be adapted to move out of the housing for causing expansion.

The means for causing the expansion of the shell comprises a series of wedges extending inwardly from each leaf defining the shell and a like plurality of slots in the core. Each slot in the core defines a slanted surface for engagement by the wedge. Upon relative movement between the leaves and the core there is caused an expansion of the leaves. The probe means is covered by a latex or plastic sleeve which is expanded upon expansion of the shell.

In one embodiment of the invention the end of the probe means that is disposed within the chamber of the housing, is preferably supported by a slidable member which is urged toward an opposite end of the housing by means of a biasing means preferably in the form of a coil spring. A water or fluid soluble body is provided at the other end of the housing. This body abuts the slideable member and thus normally maintains the probe means in its extended position. The soluble body is relatively solid at ambient room temperatures but dissolves when in contact with body fluids or mucus. Suitable waxes for such purpose include polyethylene glycol of a high molecular weight which is commercially available as Carbowax 6000 made by Union Carbide Chemicals Company (New York, N.Y.). In a modification, waxes that melt at body temperature may be used. Thus, when the dilator is inserted into the cervix over a period of time, the soluble or meltable body, which may be a wax block, dissolves or melts and the probe means is gradually extracted into the housing causing the shell to expand very gradually.

In an alternate embodiment of the invention the wax block may be in the form of an open cylinder. In still another embodiment the body is replaced by a tube that may be perforated and is gradually rolled back by a knife edge on the inside end of the probe means.

In a preferred embodiment of the present invention the dilator interconnects by a cable means to a remote actuator which comprises a housing for containing a biasing spring and a slideable member in the housing for gradually and longitudinally moving the cable means to operate the dilator by longitudinally moving the core of the dilator. Preferably, a quick disconnect is provided between the dilator and the remote actuator so that the remote actuator can be easily coupled to the dilator. The remote actuator has a control knob which is rotated to gradually open the dilator and thereafter apply a variable amount of force to the core of the dilator. The remote actuator preferably has reading scales associated therewith for indicating the degree of opening of the dilator and the amount of force being applied at the dilator.

DESCRIPTION OF THE DRAWINGS

Numerous other objects, features and advantages of the invention will now become apparent upon a reading of the following detailed description taken in conjunction with the accompanying drawings, in which:

FIG. 1 shows one embodiment of the device of the present invention;

FIG. 2 is a cross-sectional view taken along line 2—2 of FIG. 1 and showing the internal structure of the device in more detail;

FIG. 3 is a cross-sectional view taken along line 3—3 of FIG. 2;

FIG. 4 is a view similar to that shown in FIG. 3 but with the dilator expanded;

FIG. 5 is a cross-sectional view taken along line 5—5 of FIG. 2;

FIG. 6 is a somewhat enlarged fragmentary view of a portion of the device of FIG. 2 in its expanded position;

FIG. 7 is an exploded view of a portion of the device shown in FIG. 2 including the core and contact segments;

FIG. 8 is a cross-sectional view similar to that shown in FIG. 3 for a slightly different embodiment of the invention;

FIG. 9 is a cross-sectional view like that shown in FIG. 8 but with the device in its expanded position;

FIG. 10 is a fragmentary view of a portion of the device of the embodiment of FIG. 8;

FIG. 11 shows an alternate cross-sectional view of the motor drive of the invention;

FIG. 12 shows a cross-sectional view of still another embodiment of the motor drive of this invention;

FIG. 12A is a cross-section taken along the line 12A—12A of FIG. 12.

FIG. 13 is a perspective view of a system for dispensing fluid into the housing section 16 of FIG. 2;

FIG. 14 is a detail of the system shown in FIG. 13 attached to the housing;

FIG. 15 is a longitudinal cross-section of a manual expander and a dilator with which it is intended for use;

FIG. 16 is a cross-section taken on the line 16—16 of FIG. 15;

FIG. 21 is a cross-sectional view taken along line 21—21 of FIG. 20 with the dilator shown in its normal position and also in its expanded position in dotted;

FIG. 22 is a cross-sectional view taken along line 22—22 of FIG. 21; and

FIG. 23 is a cross-sectional view taken along line 23—23 of FIG. 21.

DETAILED DESCRIPTION

Figure 17:
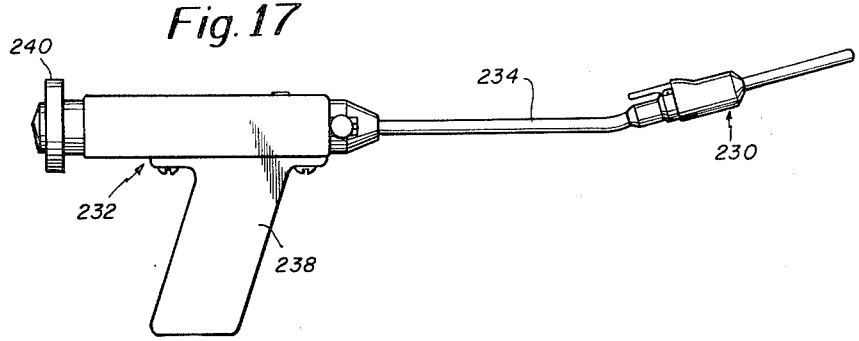
FIG. 17 shows a preferred embodiment of the dilator of this invention to be used with a remote actuator and controller.

FIG. 1 shows one embodiment of the dilator of this invention. In this embodiment the dilator comprises a probe 10, housing 12, and intermediate section 14. The housing 12 contains a motor drive arrangement which in the preferred embodiment comprises a spring and wax block. When the device is in place in the patient, the wax block melts causing the probe 10 to expand very gradually.

FIG. 2 is a cross sectional view showing the internal structure of the dilator of this invention. The housing 12 comprises a housing section 16 and barrel 18 which are interlocked by means of a bayonet-type lock comprising posts 20 which are accommodated within bayonet recesses 21 through the wall of the housing section 16. The housing section 16 also includes sidewall 22' and an end wall 22 both having apertures 24 extending therethrough to provide communication from within the chamber 25 to outside of the housing section 16.

The barrel 18 defines an open cylinder for accommodating the piston 26 which in turn defines an annular chamber 28 for accommodating the spring 30. The barrel 18 has an end wall 32 against which one end of the spring 30 rests. The other end of the spring is in the annular chamber 28 resting against wall 34. In the position shown in FIG. 2 the spring 30 is in its compressed state and is maintained in this state by means of a wax block 36 which may be of cylindrical shape and which is disposed within the chamber 25 between the wall 34 and member 38. The member 38 includes a flat plate 39 against which the wax block 36 is held, and an actuating button 40. The apertures 24 permit body fluids or other fluids to enter the chamber 25 to dissolve or melt the wax block 36 and also permit the wax to escape from the chamber 25.

The wax block 36 is as previously indicated formed of a polyethylene glycol wax. Preferably the wax block is covered with a layer of non-woven paper made of plastic fibers that are insoluble in water or body fluids. This paper sleeve provides mechanical strength and controls the velocity of the piston 26, by prolonging the rate of dissolving of the block.

On occasion the body fluids are insufficient to dissolve the wax block 36. In order to provide sufficient fluid for controlled dissolving of the block the auxiliary fluid system illustrated in FIGS. 13 and 14 is used. This auxiliary system comprises a plastic sleeve-like bag 100 that is formed with a first section 101 and a second section 102. These sections are sealed from one another by the seal 103 which may, for example, be formed by conventional heat sealing techniques in a thermoplastic material. The first section 101 is in fluid connection with the second section 102 by a valve 104. The valve 104 has one end 105 sealed within sealed strip 103. The valve 104 is formed with the knee 106 which acts when at a right angle as illustrated in FIG. 13 as a closure of the valve 104. When the knee is opened as illustrated in FIG. 14, the valve is open thus permitting fluid in the first section 101 to flow into section 102. The upper end of the sleeve-like bag is provided with flaps 107 and 108. A sheet 109 is heat sealed at its periphery to the flaps 107 and 108. This sheet 109 is made of rubber or other stretch material. An opening 110 is formed in the sheet and provides open communication with the interior or the section 102. The sheet 109 may be creased along the line 112. The sleeve-like bag is fitted over the housing section 16 with the edge of the opening 110 in engagement with the annular groove 114. Sterile fluid in section 101 is forced from that section through the valve 104 when the knee 106 has been turned to the position shown in FIG. 14. This sterile fluid may thus enter the chamber 25 through the openings 24 for prolonged dissolving of the wax block 36. If desired, a sterilization fluid may be used, such as povidone-iodine which will also function to dissolve the wax block and further functions to provide a sterile system.

The center post 42 of the piston 26 has a tapped hole for receiving one end 44 of the probe core 46. It can be seen that when the device is in place in in a patient and the block 36 dissolves, the piston 26 will move to the left as viewed in FIG. 2 and the core 46 which is affixed thereto will move in unison therewith. The piston 26 is limited in its movement in one direction by virtue of its bottoming out in the barrel 18 and is limited in the other direction by means of the retaining ring 45 which fits into a groove in the outer surface of the piston and contacts a detent 48 which prevents further movement of the piston. The detent 48 extends from the inner wall of the barrel 18.

The probe means 10 comprises, in addition to core 46, rib assembly 50 which comprises ribs 50A, 50B, 50C and 50D (see FIG. 7) and sleeve 52. The core 46 is of cylindrical shape and is provided with four longitudinal channels 54 as clearly seen in FIGS. 3-5. The channels 54 are disposed about the core 46 at equal intervals. Slots 56 extend through the core 46 between oppositely disposed channels 54. The slots 56, which in the embodiment of FIG. 2, are six in number, are defined at least in part by straight surface 59 and slanted wall 60.

The rib assembly 50 and the core 46 are probably most clearly shown in FIG. 7 in an exploded view. Each of the individual ribs comprises an elongated main arcuate member 62, three wedge elements 64, and an end tab 66 which defines with the member 62 a cut-out section 67. The wedge elements 64 may be tack welded or soldered to the inside concave surface of the member 62. Some of the wedge elements 64 are substantially flat and other ones of the wedge elements such as the two end wedge elements of rib 50C have a small interlocking flange 65. Referring now, in particular, to FIG. 6 it can be seen that opposite wedge elements 64 which are within the slot 56 are interlocked by the interlocking flange 65 as the opposite wedge elements move relative to the slanted wall 60. In FIG. 6, the probe means is shown in its expanded position.

FIG. 3 shows the ribs in their normal position with the ribs 50A and 50B held against the core 46 and the ribs 50C and 50D held against the inner ribs 50A and 50B. In this position the wedge elements 64 are fully extending into their accommodating slots 56.

In order to hold all of the ribs in place, there is provided a head 70 which is keyed by key 70A to the core 46. The keys may be a conventional keying arrangement which prevents the head 70 from rotating relative to the core but permits longitudinal movement between the core and the head. The keys 70A in the head 70 extend longitudinally of the core and are slightly skewed in this longitudinal direction to compensate for torque caused by the ribs. The head 70 may be fabricated in two halves or may snapfit into a recess provided in the barrel 18 as indicated in FIG. 2. The head is also provided with four slots or channels 72 each of which accommodates one of the tabs 66 of a rib. A cover 74 fits over the head 10 and is secured thereto by means of at least one bolt 75. The cover 74 is also provided with four slots 77, which permit the ribs to extend outwardly when they are expanded. As previously mentioned, the ribs have a cut-out section 67 that fits within the slot 77 and permits the ribs to move outwardly when expanded.

In the embodiment shown in FIGS. 1-7, the dilator is usually in the position shown in FIGS. 2 and 3 with the spring 30 under compression because of the presence of the solid wax block 36. The dilator can then be inserted into a patient and over a relatively long period of time, such as a few hours, the wax 36 dissolves. As the wax dissolves, some of the wax can escape via the ports 24 in the housing section 16. Also, as the wax block dissolves, the piston 26 can move to the left as viewed in FIG. 2 under the bias of spring 30. When this occurs the core 46 is carried with the piston but the head 70 and cover 74 are maintained stationary relative to the slowly moving core 46. The wedge elements 64 then start moving out radially. As clearly indicated in FIG. 6 the wedge elements ride on the slanted walls 60 as the core is moved and thus the ribs automatically expand outwardly to a position such as that shown in FIG. 4. As previously mentioned the wedge elements are provided with a locking edge or flange 65 so as to stabilize the rib laterally within the groove and prevent relative sliding of the opposite ribs. Because all of the slots and wedges are configured similarly, the entire rib moves in unison from one end to the other and causes a uniform expansion of the probe. The sleeve 52 is elastic and thus stretches to its expanded position as shown in FIG. 4.

It may be desired to contract the probe means even after the wax block has been partially dissolved. For this purpose there is provided the actuating button 40. This button can be pushed to slide the piston 26 to a position wherein the probe means is closed. Even if only part of the wax block is dissolved the actuating button 40 can still be used to move the piston 26 to the right as viewed in FIG. 2.

In a slightly different embodiment the head 70 may be provided in two halves each having a key associated therewith. The two halves are assembled and the cover 74 then fits over the two halves and interlocks them in place. The keys of the head fit into opposite grooves extending lengthwise of the core such as the grooves or channels 54.

In FIGS. 8-10, reference characters like those used in FIGS. 1-7 will be used where appropriate. FIG. 8 is a cross sectional view similar to that shown in FIG. 3 but for a different embodiment of the probe means. FIG. 9 shows the same embodiment in an expanded form and FIG. 10 shows a partial fragmentary view of a portion of the probe means showing a slight alteration from that previously shown. The core 46 is of substantially the same construction as shown in FIG. 3. However, the ribs 12 are of slightly different construction and have the wedge element 64 extending from one end thereof. FIG. 9 shows the probe in its expanded position. In the embodiment of FIGS. 8-10 it is preferred that the core 46 have a longitudinal axis or channel 54 and in particular, a slot for accommodating the wedge elements as shown in FIG. 10.

FIG. 11 shows an alternate to the motor drive of the preferred embodiment which uses a wax block. In FIG. 11 there is provided a housing comprising housing sections 80 and 81. In the first embodiment the wedge elements are disposed with their large end toward the housing. Alternatively, the wedge elements can be disposed in the opposite direction in which case the core would be pushed away from the housing rather than into the housing to expand the probe means. Thus, in FIG. 11 the member 82 for accommodating the spring 84 may be pushed in the direction of the arrow 85 to cause expansion of the probe means. In the embodiment of FIG. 11 there is also provided an annular shaped wax member 88 which is disposed as shown between the member 82 and the housing section 80 and under the bias of spring 84. As the wax member 88 dissolves the spring 84 causes the member 82 to move in the direction of arrow 85 causing an expansion of the probe means.

FIG. 12 shows still another arrangement comprising housing sections 89 and 90. Housing section 90 has a relatively thin metal tube 91 filled with a water soluble wax extending from one end thereof. The tube 91 may have a perforated seam or seams running longitudinal thereof. A shaft 92 which may be coupled to the core of the probe means is partially disposed in housing section 89 and has a spring 94 wound thereabout. A cutting head 95 is affixed to the end of shaft 92 and has a blade 96 for piercing the thin tube 91. The force of spring 94 causes the blade 96 to very gradually cut the tube 91 and roll back the tube preferably along a perforated edge. The tube 91 could also be constructed of a plastic material.

Referring now to FIGS. 15 and 16 there is shown a manual expander that is intended for use with the preferred embodiment of the dilator illustrated in FIG. 1. This expander is intended to be used by doctors or physicians without the wax block in order to have a manually controlled operation of the dilator. This expander permits more rapid expansion of the dilator than might be possible when the wax block 36 is used. Additionally, it permits expansion in discrete steps.

In this arrangement, the dilator consists of an elongated frame 200 which is essentially semi-cylindrical in cross-section throughout its length. At the rearward end of the expander a bearing block 201 supports the rear end of elongated shaft 202. The rearwardmost end of shaft 202 is provided with knurled head 203 adapted to be grasped and rotated by the operator. The forward end of the shaft 202 is threaded at 205 in a fixed nut 206. The nut 206 is suitably secured to the frame 200 by set screws 207 that extend through the frame 200 into the nut. The forward end of the shaft 202 is provided with a probe member 208 having a tip 209 shaped to engage the end of button 40 of the previously described dilator. Preferably the tip 209 is beveled to engage a corresponding recess in the button 40. The nut 206 is positioned in a sleeve 210 which is slidably engaged by the nut for limited reciprocal movement. The sleeve 210 is carried or actuated by arm 211 which is connected at one end to the sleeve and a hand actuator 212 which is secured to the other end of the arm 211 through a block 213. An opening 214 in the block 213 is provided so that the shaft 202 may be freely reciprocated through the block 213. The other end of the frame 200 is provided with a flange 212 adapted to engage the forward end of the dilator housing 12 and retain it within the manual expander. A suitable slot 216 is provided for the probe 10.

In operation the dilator is positioned between the flange 212 and the nut 206. The flange 212 is manually slid forwardly so that the sleeve 210 engages the rear end of the dilator to secure it within the manual expander. The operator then turns the shaft 202 so that the probe member 208 engages the button 40. The operator then by controlled rotation to the shaft 202 can force the button 40 inwardly thus causing the collapse of the probe 10 in the same manner as if the wax block 36 were used.

FIGS. 17-23 show a preferred form of the invention for remote operation of the dilator. Also, the dilator shown in this embodiment is of a slightly different form than the dilator previously shown and is a more recent development of the dilator.

Figure 18:
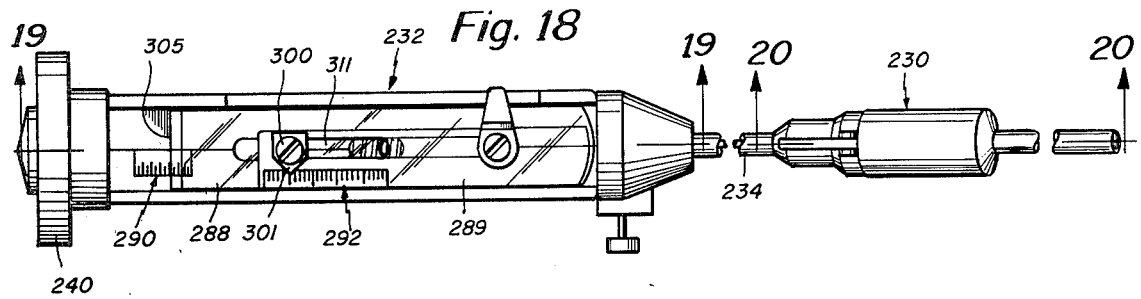
FIG. 18 is a plan view of the dilator and actuator shown in FIG. 17.
Figure 19:
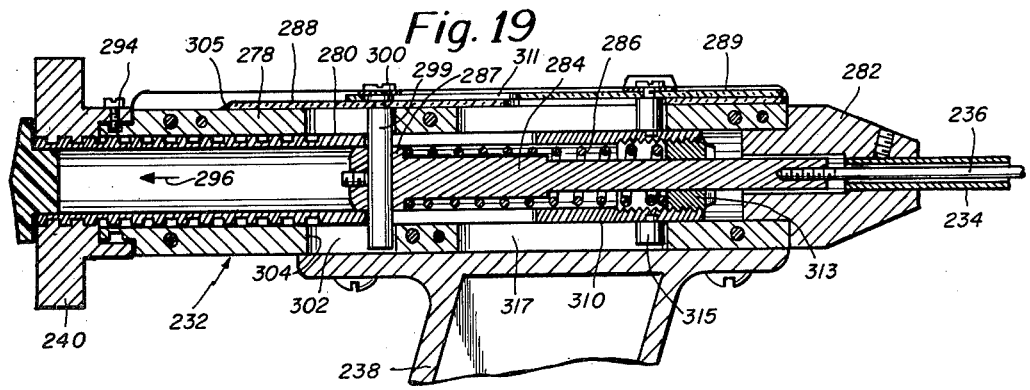
FIG. 19 is a cross-sectional view taken along line 19—19 of FIG. 18.

FIG. 17 shows the dilator 230, remote actuator 232, and coupling tube 234 which interconnects between the actuator and the dilator. As indicated in FIGS. 18 and 19, a relatively rigid cable 236 extends in the coupling tube 234 and interconnects at opposite ends to the dilator and actuator, respectively. The actuator includes a handle 238 for ease in holding the actuator, and rotatable control knob 240, the operation of which is discussed in more detail hereinafter.

The dilator of this embodiment is shown in FIGS. 20-23 and is of somewhat similar construction than the dilator previously shown in FIG. 2. This dilator comprises a housing formed by the cylindrical open member 242 cooperating with the coupling 244 attached to the end of the tube 234. The coupling 244 inserts at its end into the inside of cylindrical member 242 and has a spring loaded arm 245 associated therewith having a hooked end 246 for engaging with an aperture 247 through the wall of the cylindrical member 242. The arm 245 is biased to the position shown in FIG. 20 by a small coil spring (not shown) supported about the pivot shaft for the arm 245. In the position shown in FIG. 20 the dilator 230 is thus secured to the coupling 244.

The coupling 244 and the cylindrical member 242 define a chamber 250 in which the piston 252 is adapted to move in a longitudinal direction. The piston 252 has a threaded aperture for receiving the elongated core 254. The cylindrical member 242 is also provided with diametrically opposed slots 255 and 256 for receiving, respectively, radially extending lips 254 and 258 extending from the piston 252. This interlocking arrangement of the slots and associated lips limit movement of the piston 252 to a longitudinal direction and do not permit rotation of the piston in the cylindrical member 242.

Figure 20:
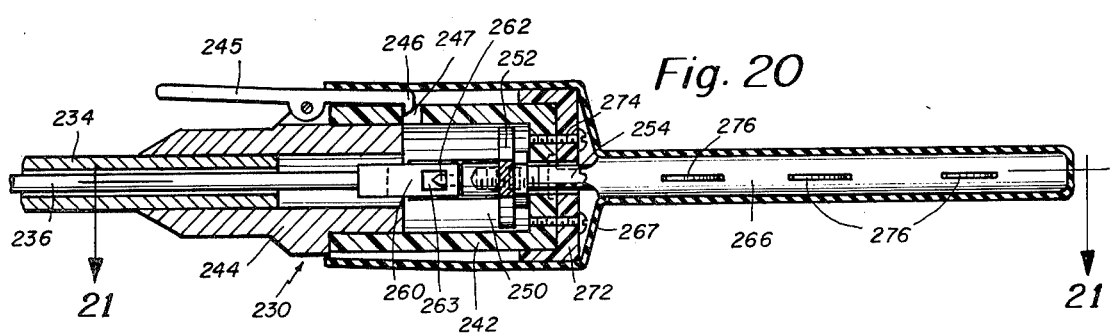
FIG. 20 is a cross-sectional view through the dilator as taken along line 20—20 of FIG. 18.

FIGS. 20 and 21 show an interlocking arrangement between the piston 252 and the rigid cable 236. The cable 236 has a bifurcated end 260 defining a pair of legs that are each slotted at 263 as shown in FIG. 21 to receive a pointed end 262 of the piston 252. In the position shown in FIG. 21 the pointed end 262 is in a locked position with the bifurcated end 260. The dilator may be disengaged from the coupling 244 by depressing the arm 245, to disengage the arm from member 242, and rotating the cylindrical member 242 through an angle of 90° relative to the coupling 244. In FIG. 21 the pointed end 262 has outwardly extending barbs 261 but these barbs are flattened on the diametrically opposed sides 259 so that upon 90° rotation the pointed end can disengage from the rigid cable 236.

In the position shown in FIGS. 20 and 21 the piston 252 is at the forward end of the housing defined by the cylindrical member 242. This is the contracted position of the probe means. When the dilator is to be expanded the cable 236 is moved to the left as viewed in FIGS. 20 and 21 and the piston 252 slides in the same direction causing an expansion of the probe means.

The probe means comprises the elongated core 254 and a pair of leaves 265 and 266 each of semi-cylindrical cross-section as depicted in FIG. 23. The shape of these leaves is shown most clearly in FIG. 21 as to their longitudinal shape. Each of these leaves includes a turned end 268 which is adapted for radial sliding within the slots 270 defined between the cap 272 and the cylindrical member 242. The cap 272 is secured to the cylindrical member by a pair of fastening screws 274 as shown in FIGS. 20 and 23. Thus, as the leaves 265 and 266 are caused to expand their ends 268 are free to move along a restricted path similar to the manner shown in FIG. 2 permitting the leaves to expand but preventing any rotational movement of the leaves relative to the core 254.

In order to provide the expanding action of the leaves, each of the leaves is provided with preferably three wedges 276 which may be integrally formed with the leaf or separately constructed and spot welded to the leaf. As most clearly shown in FIG. 23 each of the wedge elements 276 extend at their free end into a slot or passage in the opposite leaf. This arrangement provides for a maximum expansion of the leaves from a contracted position. Also, the core 254 is provided with through slots 269 for accommodating the wedge element 276. The slots 269 as shown in FIG. 21 have tapered walls 275 against which the wedge elements bear.

In operation, as the core 254 is moved into the housing defined by member 242, the wedge elements bear against the slanted walls 275 and cause the leaves 265 and 266 to expand to a position as shown in dotted in FIG. 21. It is noted in FIG. 21 that preferably the outer end of the leaves expands more than the inner end so as to assure that the device will be maintained in position in the body. This is accomplished by providing a controlled spacing between the slanted walls or a controlled spacing between the wedge elements. In the embodiment of FIG. 21 as the core is moved the rightmost wedge element engages the wall 275 first, and then the middle wedge element and then the left most wedge element. In this manner the leaves are expanded with the greatest amount of expansion occurring at the tip of the probe.

FIGS. 18 and 19 are directed to the remote actuator 232. This actuator comprises, in addition to the handle 238 and control knob 240, a cylindrical housing member 278, slide shaft 280, coupling 282, slide member 284, and compression spring 286. There are also provided a pair of transparent plates 288 and 289 which are movable longitudinally as discussed in more detail hereinafter for registering certain indications. FIG. 18 shows a first scale 290 upon which is registered an indication of expansion such as by being scaled to the diameter of the expandable probe means, and a scale 292 for indicating expansion force which is imposed by the compression of spring 286.

The control knob 240 is rotated relative to the housing member 278 to provide longitudinal movement of the rigid cable 236. A set screw 294 is provided for locking the knob 240 to the housing but permitting relative rotation between the knob and the housing member 278. In FIG. 19 the knob is shown at one extreme position with the dilator completely contracted. As the knob 240 is rotated from this initial rest position, the cylindrical slide shaft 280 moves to the left as viewed in FIG. 19 in the direction of arrow 296. The slide shaft 280 has outer threads as indicated to engage with inner threads on the rotating knob 240 to provide this action. A pin 299 is provided extending through diametrically opposed apertures in the slide shaft 280. This pin is free to move in a slot 302 in the rectangular housing member 278. The movement of the pin 299 in the slot 302 is limited by the length of the slot as shown in FIG. 19. A screw 300 is used for securing the pointer 301 to the top of pin 299. The pin 299 is also mated with the transparent plate 288 so that the plate 288 moves in unison with the movement of the pin 299. Thus, as the threaded slide shaft 280 moves in the direction of arrow 296 it compresses spring 286 by the amount of force needed to expand the dilator to a given diameter. Thus, under load conditions the relative distance between pins 300 and 315 indicates the force produced by the spring, which can be read off on scale 292 which is fixed to plate 289 and which slides by pointer 301. At the same time the edge 305 of the transparent plate 288 moves to register an indication on scale 290 as to the degree of expansion of the dilator. When the dilator has reached its maximum expansion, pin 299 has moved to the end of slot 302 and bears against the end surface 304 permitting no further movement of pin 299.

Under no load conditions the following occurs. The pin 299 is fixedly secured to the slide member 284 so that when the slide shaft 280 moves to the left, the slide member 284 is essentially fixed in position relative to the slide shaft 280. As this movement occurs the two plates 288 and 289 move together with their being no relative indication on scale 292 but with an indication as to expansion being registered on scale 290. Once the pin 299 abuts against the shoulder 304 the slide member 284 is then fixed in position but the slide shaft 280 continues to move relative to the housing member 278 as the knob 240 is further rotated. The section 310 of the slide shaft 280 continues to move in the direction of arrow 296 thereby causing the spring 286 to compress against the shoulder 287 of slide member 284. When this action occurs because of the slot 311 provided in plate 289, the plate 289 continues to move causing there to be an indication on indicator 292. This indication is for showing the force created by the compression spring 30 and acting upon the dilator by way of the rigid cable 236. The initial compression of this spring 286 may be adjusted by means of an adjusting plug 313 which may be selectively rotated to vary the compression of spring 286.

Under load conditions; that is, when there is a dilator on the instrument and the instrument is in use, the spring 286 commences to compress even with slight expansion of the dilator because of the force imposed by the body on the dilator. Thus, there is in practice a concurrent indication on both scales as the dilator is expanded. The force that must be imposed is measured on scale 292 and scale 290 shows indication of the degree of expansion of the dilator. The maximum force is reached when the pin 315 which is actually a two-piece pin comes to rest at the end of the slot 317. The slot 317 is also provided in the rectangular housing member 278.

Having described a limited number of embodiments of the present invention, it should now become apparent to those skilled in the art that numerous modifications can be made in those embodiments without parting from the spirit and scope of this invention. For example, the ribs have been shown as being of arcuate shape. Of course, these ribs could also be of other shapes such as a slightly square shape. Also, the housing members can be constructed of many different types of materials such as metal or plastic materials. Additionally, while the invention has been specifically described in the embodiment of a certical dilator, the invention is equally applicable to dilators for other purposes including non-medical dilators, as for example, tube expanders.

What is claimed is:

1. A dilator for internal body use comprising;
    an elongated probe means including an elongated core, an expandable outer shell and means associated with said core and shell for causing said shell to expand radially when the core moves longitudinally relative to said shell and in a direction away from the distal end of the shell, means defining a housing forming an at least partially closed chamber and having means for receiving an end of the probe means, means for biasing the probe means into the chamber, and a disintegratable member that is relatively solid at ambient conditions but that disintegrates upon exposure to ambient body conditions disposed to hold the probe means under bias until the dilator is inserted in the body, the biasing means thereafter causing the probe means to move gradually into the chamber with the core moving longitudinally relative to the shell away from the distal end of the shell to cause the shell to expand.

2. A dilator as set forth in claim 1 wherein said outer shell includes a plurality of elongated leaves each covering a segment of the core and having a plurality of wedges extending inwardly of the leaf.

3. A dilator as set forth in claim 2 wherein the core has a plurality of slots arranged in rows, each slot defining a slanted wall and for receiving a wedge of the leaf.

4. A dilator as set forth in claim 1 including cap means disposed on the housing adjacent the probe means and at least partially surrounding the core of the probe means and for maintaining the shell from longitudinal movement relative to the housing even when the core moves relative to the housing.

5. A dilator as set forth in claim 4 wherein the cap means includes a cap and cover and the shell includes a plurality of elongated leaves each covering a segment of the core, each leaf terminating at one end in a tab covered by the cover.

6. A dilator as set forth in claim 5 wherein the cap has radial slots for receiving the tab of each leaf.

7. A dilator as set forth in claim 1 wherein said housing comprises two sections one for housing the disintegratable member and the other for housing one end of the core of the probe means.

8. A dilator as set forth in claim 7 including a slidable member in the housing having means for receiving the biasing means and having an end of the core affixed thereto.

9. A dilator as set forth in claim 7 wherein the disintegratable member is positioned at one end of the slidable member.

10. A dilator for internal body use comprising;
an elongated probe means including an elongated core, an expandable outer shell and means associated with said core and shell for causing said shell to expand when the core and shell move relative to each other,
means defining a housing forming an at least partially closed chamber and having means for receiving an end of the probe means,
means for biasing the probe means into the chamber, and a disintegratable member that is relatively solid at ambient conditions but that disintegrates upon exposure to ambient body conditions disposed to hold the probe means under bias until the dilator is inserted in the body, the biasing means thereafter causing the probe means to move gradually into the chamber with the core moving relative to the shell to cause the shell to expand,
wherein said outer shell includes a plurality of elongated leaves each covering a segment of the core and having a plurality of wedges extending inwardly of the leaf.

11. A dilator as set forth in claim 10 wherein the core has a plurality of slots arranged in rows, each slot defining a slanted wall and for receiving a wedge of the leaf.

12. A dilator comprising a housing with at least one port therein, a longitudinally moveable probe means extending from the housing, a radially expandable shell surrounding the probe means and expandable when the probe means moves longitudinally relative to said shell, means in the housing including a soluble body for operating the probe means, a bag means separated into two sections one of which is entirely sealed and is for containing a liquid for dissolving the body, and the other of which includes an opening fitted about at least a section of the housing and valve means associated with the bag means coupled between the two sections of the bag means so that when the valve means is open the liquid in the one section flows via the other section to the housing through the said at least one aperture of the housing.

13. A dilator as set forth in claim 12 wherein the valve means includes a bendable tube extending between the bag sections.

14. In an expandable member for use in association with a body cavity having means defining a chamber and an actuating member at least partially extending into the chamber and biased toward a first position, the improvement comprising a disintegratable member disposed in the chamber and being relatively solid at a first temperature but that disintegrates upon exposure to a second greater temperature and disposed under bias when solid to maintain the actuating member in a second position, said actuating member moving to said first position as disintegratable member disintegrates.

15. In an expandable member as set forth in claim 14 wherein said actuating member includes a core biased into the chamber and adapted to move into the chamber as the member disintegrates.

16. In an expandable member as set forth in claim 15 wherein said expandable member includes a housing and an expandable outer shell about the core.

17. In an expandable member as set forth in claim 16 wherein said outer shell includes a plurality of elongated leaves each covering a segment of the core and having a plurality of wedges extending inwardly of the leaf.

18. In an expandable member as set forth in claim 17 wherein the core has a plurality of slots arranged in rows, each slot defining a slanted wall and for receiving a wedge of the leaf.

19. In an expandable member as set forth in claim 16 wherein said expandable member comprises two sections, one for housing the disintegratable member and the other for housing the actuating member.

20. A dilator for internal body use comprising;
an elongated probe means,
means including an elongated core, an expandable outer shell and means associated with said core and shell for causing said shell to expand radially when the core moves longitudinally relative to said shell,
means defining a housing forming an at least partially closed chamber and having means for receiving an end of the probe means,
means for biasing the probe means in a first direction in the chamber,
and a disintegratable member that is relatively solid at a first temperature but that disintegrates upon exposure to a second greater temperature disposed to hold the probe means under bias while at said first temperature, said biasing means thereafter causing the probe means to move gradually to a second position of said chamber to cause operation of said probe means.

21. In an expandable member as set forth in claim 14 wherein said actuating member is supported for longitudinal movement.

* * * * *